United States Patent [19]
Ashton et al.

[11] Patent Number: 4,859,680
[45] Date of Patent: Aug. 22, 1989

[54] PYRIMIDINE DERIVATIVES AS ANTIVIRAL COMPOUNDS

[75] Inventors: Wallace T. Ashton, Clark, N.J.; Edward Walton, Sun City West, Ariz.; Richard L. Tolman, Warren, N.J.

[73] Assignee: Merck & Co., Inc., Rahway, N.J.

[21] Appl. No.: 157,076

[22] Filed: Feb. 4, 1988

Related U.S. Application Data

[63] Continuation of Ser. No. 889,014, Jul. 24, 1986, abandoned, which is a continuation-in-part of Ser. No. 598,612, Apr. 10, 1984, Pat. No. 4,617,304.

[51] Int. Cl.4 .................. A61K 31/505; C07D 239/10
[52] U.S. Cl. .................................... 514/274; 544/317; 544/318
[58] Field of Search ................. 544/317, 318; 514/274

[56] References Cited

U.S. PATENT DOCUMENTS 4,617,304 10/1986 Ashton et al. ...................... 514/261

OTHER PUBLICATIONS

Khare et al., Proc. Soc. Exp. Biol. & Med., 140, pp. 880-884 (1972).
Rada & Doskocil, Pharmacol. & Therap., 9, pp. 171-217 (1980).

Primary Examiner—Mary C. Lee
Assistant Examiner—Zinna Northington
Attorney, Agent, or Firm—Richard S. Parr; Hesna J. Pfeiffer

[57] ABSTRACT

Pyrimidines having a fused cyclopropane ring in the side chain and the heterocyclic isosteres of said pyrimidines, which have antiviral activity, especially against viruses of the herpes class.

8 Claims, No Drawings

PYRIMIDINE DERIVATIVES AS ANTIVIRAL COMPOUNDS

This is a continuation of application Ser. No. 889,014, filed July 24, 1986, now abandoned, which application is a continuation-in-part of U.S. patent application Ser. No. 598,612, filed Apr. 10, 1984, U.S. Pat. No. 4,617,304, issued Oct. 14, 1986.

BACKGROUND OF THE INVENTION

The present invention relates to hydroxyalkyl-substituted pyrimidines having a fused cyclopropane ring in the hydroxyalkyl side chain and the heterocyclic isosteres of said pyrimidines, and to processes for preparing such compounds. These compounds have antiviral acitivity, and are particularly effective against herpes viruses, e.g., herpes simplex virus.

The compounds of the invention may be represented by the formula,

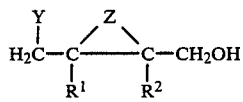

(and the pharmaceutically acceptable salts thereof), wherein Y is a pyrimidin-1-yl or a hetercyclic isostere of a pyrimidin-1-yl group; $R^1$ is selected from hydrogen and alkyl of 1-to-4 carbon atoms; $R^2$ is selected from hydrogen, alkyl of 1-to-4 carbon atoms and —CH$_2$OH; and Z is >CH$_2$ or >O.

Preferably, Y is cytosine, uracil or thymine.

An isostere is a molecule which is isosteric with another molecule; that is, has a similarity of structure and a resulting similarity of properties exhibited by the molecules. The molecules may contain different atoms and not necessarily the same number of atoms, but possess the same total or valence selections in the same arrangement, viz., carbon monoxide (C=O) and atmospheric nitrogen (N=N), or cyanide ion (—C≡N) and acetylide ion (—C≡CH). Some heterocyclic systems isosteric with oxopyrimidines include 3-deazauracil (e.g. 2,4-dihydroxypyridine), 6-azauracil (e.g. 3,5-dihydroxy-1,2,4-triazine), and 5-azacytosine (2-amino-4-hydroxy-1,3,5-triazine).

The following are representative compounds of the present invention:
1-[(E)-2-(Hydroxymethyl)cyclopropylmethyl]thymine
1-[(Z)-2-(Hydroxymethyl)cyclopropylmethyl]thymine
1-[(E)-2-(Hydroxymethyl)cyclopropylmethyl]uracil
1-[(Z)-2-(Hydroxymethyl)cyclopropylmethyl]uracil
1-[(E)-2-(Hydroxymethyl)cyclopropylmethyl]cytosine
1-[(Z)-2-(Hydroxymethyl)cyclopropylmethyl]cytosine
1-[2,2-Bis(hydroxymethyl)cyclopropylmethyl]thymine
1-[2,2-Bis(hydroxymethyl)cyclopropylmethyl]uracil
1-[(E)-2,3-Epoxy-4-hydroxybutyl]thymine
1-[(Z)-2,3-Epoxy-4-hydroxybutyl]thymine
1-[(E)-2,3-Epoxy-4-hydroxybutyl]uracil
1-[(Z)-2,3-Epoxy-4-hydroxybutyl]uracil
1-[(E)-2-Hydroxymethyl-1,2-dimethylcyclopropylmethyl]thymine
1-[(Z)-2-Hydroxymethyl-1,2-dimethylcyclopropylmethyl]thymine
1-[(E)-2-Hydroxymethyl-1,2-dimethylcyclopropylmethyl]uracil
1-[(Z)-2-Hydroxymethyl-1,2-dimethylcyclopropylmethyl]uracil
1-[(E)-2-(Hydroxymethyl)cyclopropylmethyl]cytosine
1-[(Z)-2-(Hydroxymethyl)cyclopropylmethyl]cytosine
1-[(2,2)-Bis(hydroxymethyl)cyclopropylmethyl]cytosine
1-[(E)-2,3-Epoxy-4-hydroxybutyl]cytosine
1-[(Z)-2,3-Epoxy-4-hydroxybutyl]cytosine
1-[(E)-2-Hydroxymethyl-1,2-dimethylcyclopropylmethyl]cytosine, and
1-[(Z)-2-Hydroxymethyl-1,2-dimethylcyclopropylmethyl]cytosine.

The following compounds are preferred:
1-[(Z)-2-(Hydroxymethyl)cyclopropylmethyl]thymine
1-[(Z)-2-(Hydroxymethyl)cyclopropylmethyl]uracil
1-[(Z)-2-(Hydroxymethyl)cyclopropylmethyl]cytosine The compounds of the present invention may be prepared by various methods, as represented by the following schemes:

Scheme I

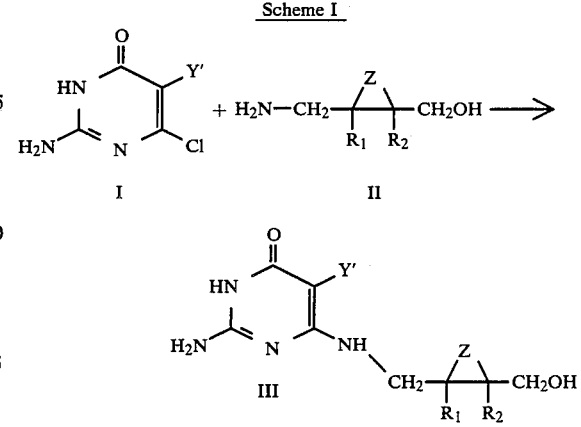

Scheme II

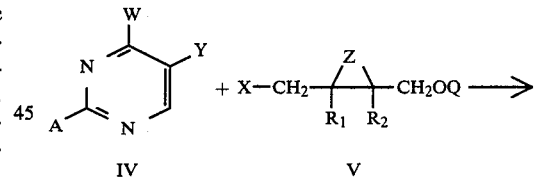

Scheme III

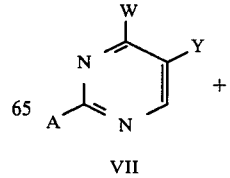

-continued
Scheme III

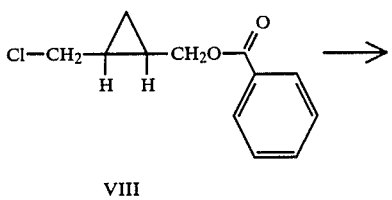

VIII

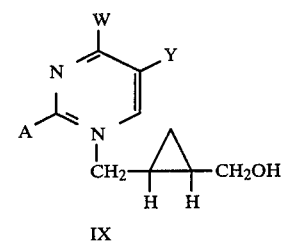

IX

According to one method (Scheme I), which is similar to that of Noell et al., *J. Med. Pharm. Chem.*, 5, 558 (1962), 6-chloroisocytosine [2-amino-6-chloro-4(3H)-pyrimidinone], a compound within the genus of Formula I, is reacted with an excess amount of the appropriate amino alcohol of Formula II. The reaction is conducted at elevated temperature in a suitable high boiling, polar solvent, preferably 2-ethoxyethanol, at reflux. Preferably, about three equivalents of the compound of Formula II are used per equivalent of the compound of Formula I, but a lesser amount of the compound of Formula II, preferably from about 1.5 to 2 equivalents, may be used if a compatible base, such as a high-boiling tertiary aliphatic amines, e.g., 1,4-diazabicyclo[2.2.2]-octane (DABCO), is added to the reaction mixture to scavenge the HCl liberated during the reaction. The reaction is run for from about 1 to about 18 hours, preferably for from about 1 to about 3 hours, and the resulting 6-(hydroxyalkylamino)isocytosine of Formula III may be isolated.

Isosteres of compounds of Formula III may then be prepared by known methods.

The 1-substituted pyrimidines of Formula VI may also be prepared (Schemes II) by alkylation of a preformed pyrimidine derivative of Formula IV (e.g., 5-azacytosine, pertrimethylsilyl-uracil, pertrimethylsilyl-thymine, 2,4-dimethoxypyrimidine, or $N^4$-acetylcytosine) with a compound of Formula V, wherein X is a leaving group, such as bromo, chloro, iodo, tosyl, mesyl and the like, and Q is a protecting group removable by hydrolysis, such as, for example, benzoyl or acetyl, or by hydrogenolysis such as, for example, benzyl. The alkylation may be carried out in the presence of a base such as, for example, potassium carbonate or sodium hydride, in a suitable solvent such as, for example, dimethylformamide or dimethylsulfoxide, or it may be carried out in these solvents without additional base. The 1-alkylated product of Formula VI may be separated from any isomers chromatographically or by other means. Transformation of the substituents Z and W, and removal of the protecting group Q may be accomplished by standard methods known to those skilled in the art.

Scheme III then illustrates the preparation of, e.g., 1-[(Z)-2-(hydroxymethyl)cyclopropylmethyl]cytosine, by the addition of chloromethylcyclopropane VIII to a pyrimidine of Formula VII. Chloromethylcyclopropanes may also be used to alkylate other pyrimidines of this invention or other isosteric heterocyclic systems. Such alkylations may be accomplished in the presence of sodium iodide and a base, such as potassium carbonate, in a polar solvent, such as dimethyl sulfoxide or dimethyl formamide, preferably at a temperature of about 70° to 90° C. The resulting alkylated pyrimidines may then be purified by chromatography and the benzoyl protecting group may be removed by standard conditions, such as aqueous methylamine, methanolic ammonia, or catalytic sodium methoxide in methanol.

Synthetic scheme II is also readily amenable to the synthesis of isosteric oxypyrimidine compounds by simply substituting the appropriately-preformed isosteric heterocycle for the oxypyrimidine which undergoes the alkylation reaction.

Pharmaceutically-acceptable salts are prepared by recrystallization of the desired cytosine, uracil or thymine derivative as the free base or as the acetate or hydrochloride from the aqueous dilute acid of choice. Alkali metal salts of thymine and uracil derivatives may be made by standard techniques, for example, by dissolving such derivative in water containing one equivalent of an alkali metal hydroxide, followed by evaporation to dryness.

In another aspect of the invention there is provided a pharmaceutical composition or preparation comprising a compound of the formula

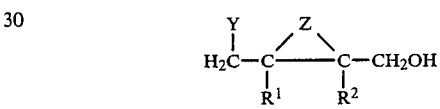

wherein Y, Z, $R^1$ and $R^2$ are as hereinbefore defined; or a pharmaceutically-acceptable salt thereof, together with a pharmaceutically-acceptable carrier therefor. In a particular aspect the pharmaceutical composition comprises a compound of the present invention in effective unit dosage form.

As used herein the term "effective unit dosage" or "effective unit dose" is denoted to mean a predetermined antiviral amount sufficient to be effective against the viral organisms in vivo. Pharmaceutically-acceptable carriers are materials useful for the purpose of administering the medicament, and may be solid, liquid or gaseous materials, which are otherwise inert and medically acceptable and are compatible with the active ingredients.

These pharmaceutical compositions may be given parenterally, orally, used as a suppository or pessary, applied topically as an ointment, cream, aerosol, powder, or given as eye or nose drops, etc., depending on whether the preparation is used to treat internal or external viral infections.

For internal infections the compositions are administered orally or parenterally at dose levels of about 0.1 to 250 mg per kg, preferably 1.0 to 50 mg per kg of mammal body weight, and are used in man in a unit dosage form, administered, e.g. a few times daily, in the amount of 1 to 250 mg per unit dose.

For oral administration, fine powders or granules may contain diluting, dispersing and/or surface active agents, and may be presented in a draught, in water or in a syrup; in capsules or sachets in the dry state or in a non-aqueous solution or suspension, wherein suspending agents may be included; in tablets, wherein binders and lubricants may be included; or in a suspension in water or a syrup. Where desirable or necessary, flavoring, preserving, suspending, thickening or emulsifying agents may be included. Tablets and granules are preferred, and these may be coated.

For parenteral administration or for administration as drops, as for eye infections, the compounds may be presented in aqueous solution in a concentration of from about 0.1 to 10%, more preferably 0.1 to 7%, most preferably 0.2% w/v. The solution may contain antioxidants, buffers, etc.

Alternatively, for infections of the eye, or other external tissues, e.g. mouth and skin, the compositions are preferably applied to the infected part of the body of the patient as a topical ointment or cream. The compounds may be presented in an ointment, for instance, with a water soluble ointment base, or in a cream, for instance with an oil in water cream base, in a concentration of from about 0.1 to 10%, preferably 0.1 to 7%, most preferably 1% w/v.

The following examples illustrate the present invention without, however, limiting the same thereto. All ingredients are expressed in degrees Celsius.

EXAMPLE 1

(Z) and (E)-6-(Hydroxymethyl) cyclopropylmethylamino-5-nitrosoisocytosine

Step A-1: Ethyl trans- and cis-2-cyanocyclopropanecarboxylate ((E) and (Z) respectively)

These materials were prepared essentially according to the procedure of V. I. Ivanskii and V. N. Maksimov, *J. Org. Chem. U.S.S.R.*, 8, 54 (1972). Acrylonitrile (38 g.) was stirred under reflux in an oil bath as ethyl diazoacetate (40 g.) was added portionwise over a period of 2.5 hours. After completion of the addition, the mixture was stirred at reflux for an additional 1.5 hours. The excess acrylonitrile was then removed by distillation. The temperature was raised to 125°-130° and maintained there until nitrogen evolution ceased (about 2 hours). Finally, the mixture was heated at 160°-170° for 0.5 hours. After cooling to room temperature overnight under nitrogen, the material was distilled in vacuo. Two major fractions were collected. Fraction 1 was collected at 95°-100° (4.75 mm) and amounted to 17.2 g. of colorless liquid. Fraction 2 was collected at 110°-122° (4.75 mm) and then at 80°-90° (0.5 mm). After filtering to remove a white solid contaminant, fraction 2 amounted to 12 g. Whereas fraction 1 was homogeneous by TLC (1:1 hexane-ethyl acetate), fraction 2 was impure. Fraction 2 was thus subjected to preparative HPLC (silica gel, 7:3 hexane-ethyl acetate, refractive index detection, 3 cycles). Chromatographic fractions containing clean product (lower Rf than fraction 1 on silica gel TLC) were combined and concentrated in vacuo to give 8.53 g of colorless liquid. NMR studies, including proton decoupled $^{13}C$ NMR confirmed that the lower-boiling product (distillation fraction 1) was the trans-isomer, while the higher-boiling product (purified material from distillation fraction 2) was the cis-isomer. Ivanskii and Maksimov reported a boiling point of 82°-83° (5 mm) for the trans-isomer and did not report isolation of the cis-isomer. R. D. Allan, D. R. Curtis, P. M. Headley, G. A. R. Johnston, D. Lodge, and B. Twitchin, *J. Neurochem.*, 34, 652 (1980) obtained both the trans- and cis-isomers by this method and separated them by fractional distillation, but no boiling points or other physical properties were given.

The following is an alternative synthesis of the cis-isomer ((Z)):

Step A-2: Ethyl (Z)-2-cyanocyclopropanecarboxylate

This material was prepared essentially according to the method of V. I. Ivanskii, I. A. D'yakonov, and T. M. Gundalova, *J. Org. Chem. U.S.S.R.*, 3, 1302 (1967) and L. L. McCoy, *J. Org. Chem.*, 25, 2078 (1960). A suspension of 8.4 g. (200 mmole) of sodium hydride (57% in oil) in 40 ml of toluene was stirred mechanically under a nitrogen blanket with intermittent cooling in an ice bath to maintain an internal temperature of 15°-20°. To this was added dropwise, over a period of 20 minutes, a mixture of 10.6 g. (20 mmole) of acrylonitrile and 24.5 g. (200 mmole) of ethyl chloroacetate. After about 1 hour at room temperature, the reaction mixture was warmed to 45°-55°. After 1 hour at this temperature, 1.0 ml of methanol was added dropwise, resulting in vigorous gas evolution, darkening, and a slight exotherm. After an additional 3 hours, 10.2 ml of absolute ethanol was added dropwise, leading initially to vigorous foaming and a brief exotherm to about 70°. After cooling and stirring overnight at room temperature, the mixture was partitioned between ethyl acetate and $H_2O$. The ethyl acetate fraction was washed further with $H_2O$, then dried over magnesium sulfate, treated with charcoal, and filtered through Super-Cel. Concentration of the filtrate gave a residual oil consisting of two liquid phases. This material was further partitioned between methanol and pentane to remove mineral oil. Evaporation of the methanol fraction gave 10.8 g, of orange-brown oil, which was vacuum-distilled through a Vigreux column. The purest material (1.71 g of colorless liquid) was collected at 85°-88° (0.7 mm), although additional material of somewhat lesser purity was collected at 77°-85° (0.7 mm) (1.87 g) and at greater than 94° (0.7 mm) (0.54 g.). The material was identical by NMR, IR, and TLC (thin layer chromatography) to the higher-boiling product (identified as the cis-isomer) from the reaction of acrylonitrile with ethyl diazoacetate. This result casts doubt on the suggestion by Ivanskii, D'yakonov, and Gundalova that the ethyl 2-cyanocyclopropanecarboxylate obtained from the base-induced reaction of acrylonitrile with ethyl chloroacetate may be the trans-isomer. The result is consistent, however, with McCoy's observations that the cis-isomer normally predominates in this type of reaction.

Step B-1: (Z)-2-(Aminomethyl)cyclopropanemethanol

A mixture of 3.42 g (90 mmole) of lithium aluminum hydride and 100 ml of dry tetrahydrofuran was stirred at gentle reflux under nitrogen as a solution of 8.35 g (60 mmole) of ethyl (Z)-2-cyanocyclopropanecarboxylate in 20 ml of tetrahydrofuran was introduced dropwise over a period of about 2 hours. After an additional 2 hours, the reaction was cooled. The mixture was stirred in an ice bath and maintained under nitrogen as 20 ml of water was added dropwise with caution at such a rate that the temperature remained below 20°. During the first part of the addition, there was vigorous gas evolution, followed by heavy precipitation. After stirring for several minutes, the precipitated solid was removed by filtration and washed with tetrahydrofuran. The combined filtrate and washings were dried over sodium sulfate, then filtered, and concentrated by rotary evaporation. The residual oil was distilled through a shortpath apparatus to give 3.67 g (60%) of colorless liquid, bp 51°–58° (0.2 mm). A boiling point of 55°–58° (0.1 mm) was reported for this compound by J. G. Cannon, A. B. Rege, T. L. Gruen, and J. P. Long, *J. Med. Chem.*, 15, 71 (1972). The material showed satisfactory purity by TLC (70:30:3 chloroform-methanol-concentrated ammonium hydroxide), and the structure was confirmed by NMR.

Step B-2: (E)-2-(Aminomethyl)cyclopropanemethanol

This compound, prepared analogously to the (Z)-isomer, was obtained in 53% yield as a pale yellow, somewhat viscous oil, bp 79°–82° (1.2–1.4 mm). A boiling point of 51° (0.5 mm) was reported for this compound by J. G. Cannon, A. B. Rege, T. L. Gruen, and J. P. Long, *J. Med. Chem.*, 15, 71 (1972). The material showed satisfactory purity by TLC (70:30:3 chloroform-methanol-concentrated ammonium hydroxide), and the structure was confirmed by NMR.

Step C-1:
6-[(Z)-2-(Hydroxymethyl)cyclopropylmethylamino]-5-nitrosoisocytosine

A solution of 3.28 g (20 mmole) of 6-chloroisocytosine monohydrate, 3.54 g (35 mmole) of (Z)-2-(aminomethyl)cyclopropanemethanol, and 1.12 g (10 mmole) of 1,4-diazabicyclo[2.2.2]octane in 9 ml of 2-ethoxyethanol was stirred at reflux under nitrogen. After 2.5 hours the solution was cooled and concentrated on a rotary evaporator under high vacuum. The residual gum was dissolved with heating in 15 ml of glacial acetic acid, then diluted with 10 ml of water, and cooled in ice. The solution was then stirred at ambient temperature as a solution of 2.76 g (40 mmole) of sodium nitrite in 15 ml of water was added. The resulting solution immediately turned dark, followed rapidly by thick precipitation and foaming. The foaming gradually subsided. After about 2 hours, the precipitated solid was collected on a filter and washed thoroughly with water, then with acetone, to give 1.28 g of orange powder, mp 228.5°–229° dec. TLC (80:20:2 chloroform-methanol-water) showed a trace of impurity at the origin. An analytical sample (light orange crystals, mp 234°–235° dec.) was obtained by recrystallization from water. The structure was confirmed by NMR.

Analysis calculated for $C_9H_{13}N_5O_3$: C, 45.18; H, 5.48; N, 29.28. Found: C, 45.35; H, 5.61; N, 29.26.

Step C-2:
6-[(E)-2(Hydroxymethyl)cyclopropylmethylamino)-5-nitrosoisocytosine

This compound, prepared analogously to the (Z)-isomer, was obtained as orange-tan crystals, mp 227°–228° dec. The material showed satisfactory purity by TLC (80:20:2 chloroform-methanol-water), and the structure was verified by NMR.

Analysis calculated for $C_9H_{13}N_5O_3 \cdot H_2O$: C, 42.02; H, 5.88; N, 27.23. Found: C, 42.15; H, 5.57; N, 27.26.

EXAMPLE 2

1-[2,2-Bis(hydroxymethyl)cyclopropylmethyl]uracil

Step A: 1,1-Bis(hydroxymethyl)-2-vinylcyclopropane

A solution of 23 g (0.108 mole) of diethyl 2-vinylcyclopropane-1,1-dicarboxylate in 90 ml of dry THF (tetrahydrofuran) was added dropwise to 196 ml of 1M LAH (lithium aluminum hydride) which was stirred and heated at 68°. The addition required 30 minutes and heating and stirring were continued for 2 hours. TLC in cyclohexane-ethyl acetate (1:1) and $CHCl_3$ MeOH (9:1) showed that the reaction was complete. The reaction was cooled to 0° and a total of 200 ml of water was continuously added. After being stirred for 15 minutes, the mixture was filtered and the solid was washed with THF. The combined filtrates were concentrated to yield 12.9 g (93%) of the title compound, $R_f$ $CHCl_3$-MeOH (9:1) 0.45.

NMR ($CDCl_3$) δ: 5.89 (oct, 1H, J=8, 10, 16.5 Hz), 5.36 (oct, 1H, J=16.5, 2, 0.8 Hz), 5.24 (oct 1H, J=10, 2, 0.6 Hz), 3.98, 3.74 (q, 2H; J=14 Hz), 3.74 (s, 2H), 1.58–1.70 (m, 1H), 0.88 (dd, 1H, J=8.5 and 5.5 Hz), 0.69 (tr, 1H, J=5.5 Hz).

Step B:
1,1-Bis(benzoyloxymethyl)-2-vinylcyclopropane

A solution of 5.5 g (43 mmoles) of 1,1-bis(hydroxymethyl)-2-vinylcyclopropane in 40 ml of pyridine was cooled to 0° and 18.5 g (130 mmoles; 15.2 ml) of benzoyl chloride was added dropwise over 15 minutes. The mixture was stirred at 22° for 2 hours. TLC in cyclohexane-EtOAc (4:1) indicated that the reaction was complete. The reaction mixture was treated with 8 ml of water and stirred at 22° for 20 hours. It was concentrated to a residual oil and redissolved in 150 ml of EtOAc and washed with 50 ml of water, three 50-ml portions of 2N HCl, four 50 ml portions of saturated $NaHCO_3$, dried ($MgSO_4$), filtered and concentrated to give 11 g (75%) of the title compound, $R_f$ cyclohexane-ethyl acetate (4:1) 0.7.

NMR ($CDCl_3$) δ: 7.36–8.04 (m, 10H), 5.78 (oct 1H, J=17, 10, 7.5 Hz), 5.24 (oct 1H, J=17, 1.7, 1 Hz), 5.51 (oct 1H, J=10, 1.6, 0.8), 4.29, 4.65 (q, 2H, J=12 Hz), 4.13, 4.23 (q, 2H, J=11.5 Hz), 2.80–2.92 (m, 1H), 1.12, 1.17 (dd, 1H, J=8.5, 5.5 Hz), 0.98 (Tr, 1H, J=5.5 Hz).

Step C:
1,1-Bis(benzoyloxymethyl)-2-hydroxymethylcyclopropane

A solution of 11 g (33 mmoles) of 1,1-bis(benzoyloxymethyl)-2-vinylcyclopropane in 200 ml of $CH_2Cl_2$ was cooled to −70° and stirred while a stream of $O_3$ was introduced over a period of 30 minutes, at which time a permanent blue color was obtained. TLC in cyclohexane-ethyl acetate (4:1) indicated that the starting material was no longer present and several new more polar products ($R_f$ 0.55, 0.5, 0.47, 0.4) had been formed. The reaction mixture was treated with 6.6 g (174 mmoles) of $NaBH_4$ and the cooling bath was removed. Stirring was continued for 1.5 hours and TLC showed the formation of a more polar ($R_f$ 0.2) product. The reaction mixture was acidified by the continuous dropwise addition of 200 ml of 2N HCl. The mixture was concentrated to remove the $CH_2Cl_2$ and the aqueous layer was extracted with three 100 ml portions of EtOAc which was washed with 50 ml of water, 100 ml of saturated $NaHCO_3$ and 50 ml of saturated NaCl. The EtOAc layer was dried ($MgSO_4$), filtered and concentrated to give 11.3 g of crude product which was chromatographed on 600 ml of silica gel; first eluting with 2400 ml of cyclohexane-ethyl acetate (5:2) and finally with 1600 ml of 2:1 cyclohexane ethyl acetate. Fractions containing only product were combined and concentrated to give 4 g (36%) of the desired compound.

NMR ($CDCl_3$): 8.00–8.10 (m, 10H), 4.32, 4.86 (q, 2H, J=12.5 Hz), 4.30, 4.42 (q, 2H, J=12 Hz), 3.61, 3.97 (ABX oct, 2H, $J_{AB}$ 12 Hz, $J_{AX}$ 5.5 Hz, $J_{BX}$=9 Hz), 2.35

(s, br, 1H), 1.46–1.62 (m, 1H), 1.02, 1.07 (dd, 1H, J=9 and 5.5 Hz), 0.70 (tr, 1H, J=5.5 Hz).

Step D:
1,1-Bis(benzoyloxymethyl)-2-toluenesulfonyloxymethylcyclopropane

A solution of 4.5 g (13.2 mmole) of 1,1-bis(benzoyloxymethyl)-2-hydroxymethylcyclopropane in 50 ml of dry pyridine was treated with 7 g (37 mmoles) of p-tosyl chloride and stirred at 22° for 1.5 hours. TLC in cyclohexane-ethyl acetate (2:1) ($R_f$ 0.6) indicated that the reaction was complete. The reaction was concentrated and the residue was dissolved in 150 ml of EtOAc and washed with 50 ml of water, 100 ml saturated NaHCO$_3$, four 250 ml portions of water and 50 ml of saturated NaCl. The ethyl acetate layer was dried (MgSO$_4$), filtered and concentrated to 9 g of residual solid. The crude product was chromatographed on 500 ml of silica gel in cyclohexane-ethyl acetate (5:1). Fractions containing only product were combined and concentrated to give 3.36 g (54%) of the title compound.

NMR (CDCl$_3$) δ: 7.22–8.06 (m, 14H), 4.18, 4.68 (q, 2H, J=12 Hz), 4.06, 4.38 (ABX oct, 2H, $J_{AB}$=11 Hz, $J_{AX}$=7 Hz, $J_{BX}$=9 Hz), 8.29 (s, 1H), 2.41 (s, 1H), 1.46–1.62 (m, 1H), 1.07, 1.12 (dd, 1H, J=9 Hz and 5.5 Hz), 0.76 (tr, 1H, J=5.5 Hz).

Step E:
1-[2,2-bis(benzoyloxymethyl)cyclopropylmethyl]uracil

A solution of 3.36 g (6.8 mmoles) of 1,1-bis(benzoyloxymethyl)-2-p-toluenesulfonyloxymethylcyclopropane in 15 ml of dry DMF (dimethylformamide) is added to 8.2 mmoles of bis-2,4-trimethylsislyloxypyrimidine in 20 ml of DMF and the mixture is heated to 60° and stirred for 4 hours, with methanol and 1M sodium bicarbonate being added in equal portions. The mixture is then concentrated and the residue dissolved in 60 ml of CHCl$_3$-MeOH (1:1) and filtered. About 20 ml of silica gel is added and the mixture is concentrated to dryness, with the residue being added to the top of a 200 ml silica gel column and chromatographed in CMW (chloroform-methanol-water) (97.5:2.5:0.15). Fractions containing the product are then pooled and concentrated to give the title compound.

Step F:
1-[2,2-Bis(hydroxymethyl)cyclopropylmethyl]uracil

A suspension of 3.62 mmoles of 1-[2,2-bis(benzoyloxymethyl)-1-cyclopropylmethyl]uracil in 178 ml of 2.5N HCl is stirred at 100° for about 5 hours. The reaction mixture is concentrated to a residual semi-solid which is triturated with three 20 ml portions of Et$_2$O and dried, and the residue is dissolved in 5 ml of water and neutralized (pH 7) with 2N NaOH. The solid separates and is removed and dried, and the filtrate is concentrated to dryness. The solids are then combined, dissolved in a small amount of CHCl$_3$-MeOH (1:1) and put on five 2000 micron preparative TLC plates which are developed in CMW (70:30:3). The product bands ($R_f$ 0.3) are eluted with CHCl$_3$-MeOH (3:2) and when concentrated yield the titled product.

EXAMPLE 3
1-[(Z)-2,3-Epoxy-4-hydroxybutyl]thymine

Step A: 4-Benzoyloxy-2,3-cis-epoxybutanol

A solution of 3.34 g (20 mmoles) of cis-2-butene-1,4-diol monobenzoate in 60 ml of CHCl$_3$ was mixed with 3.45 g (20 mmoles; 4.3 g of 80%) m-chloroperbenzoic acid. The mixture was stirred and warmed to 40°. The reaction was monitored by TLC in cyclohexane-EtOAc (3:2) ($R_f$ 0.5 (starting material), 0.35 (product)) and was complete in 4 hours. The reaction mixture was diluted with 100 ml of CHCl$_3$ and washed with saturated NaHCO$_3$ to remove m-chlorobenzoic acid. It was washed with saturated NaCl, dried (MgSO$_4$), filtered and concentrated to yield a residue of 4.1 g (98%) of the title compound, an oil which solidified on standing.

NMR (CDCl$_3$) δ: 7.42–8.12 (m, 5H), 4.58, 4.36 (ABX oct, 2H, $J_{AB}$=12 Hz, $J_{AX}$=5.3 Hz, $J_{BX}$=5.3 Hz) 3.92 (d, 2H, J=5.5 Hz), 3.18–3.42 (m, 2H).

Step B: 4-Benzoyloxy-2,3-cis-epoxybutyl α-toluenesulfonate

A solution of 3.08 g (10 mmoles) of 4-benzoyloxy-2,3-cis-epoxybutanol in 30 ml of pyridine was cooled to 0° and treated with 4.7 g (25 mmoles) of alpha-toluenesulfonyl chloride and stirred. The cooling bath was removed and as the temperature rose the reaction became very dark. TLC in cyclohexane-ethyl acetate (2:1) ($R_f$ 0.3 (starting material); 0.6 (product)) indicated that the reaction was complete in 15 minutes. The reaction mixture was concentrated at 30° to remove most of the pyridine and the residue was dissolved in 100 ml of EtOAc. The EtOAc solution was washed with 25 ml of water, 50 ml of 2N HCl, 25 ml of saturated NaHCO$_3$, 25 ml of saturated NaCl and dried (MgSO$_4$), filtered and concentrated to 3.3 g of residual oil. The crude product was chromatographed on 250 ml of silica gel in cyclohexane-EtOAc (4:1). Fractions containing only product were combined and concentrated to yield 1.61 g (45%) of the title compound.

NMR (CDCl$_3$) δ: 7.32–8.08 (m, 10H), 4.28, 4.44 (ABX oct, 2H, $J_{AB}$=13.5 Hz, $J_{AX}$=4.8 Hz, $J_{BX}$=6.0 Hz), 4.14, 4.32 (ABX oct, 2H, $J_{AB}$=12.0 Hz, $J_{AX}$=4.5 Hz, $J_{BX}$=7.2 Hz), 3.39, 3.42 (2 tr, 2H, J=4.5 Hz, J'=4.3 Hz), 3.26, 3.30 (2 tr, 1H, J=4.5 Hz, J=4.2 Hz).

Step C: 1-(4-benzoyloxy-2,3-cis-epoxybutyl)thymine

A solution of 2.5 mmoles of pertrimethylsilylthymine 10 ml of dry DMF is stirred and cooled to 0°. A solution of 830 mg (2.29 mmoles) of 4-benzoyloxy-2,3-bis-epoxybutyl α-toluenesulfonate in 5 ml of DMF and the mixture is heated at 45°. After thirty minutes a mixture of methanol and 1M sodium bicarbonate is added and the reaction is concentrated and the residue washed four times with 4 ml of ether, then centrifuged and dried. The resulting solid is washed four times with 4 ml of water and dried, with recrystallization from methanol giving the title compound.

Step D: 1-[Z-2,3-epoxy-4-hydroxybutyl)]thymine

A suspension of 0.92 mmole of 1-(4-benzoyloxy-2,3-cis-epoxybutyl)thymine in 20 ml of MeOH is stirred at 22° and 10 mg of Na is added, with additional MeOH and sodium being added if necessary. After the product has precipitated and the reaction is complete, the mixture is concentrated, cooled and centrifuged, and the precipitate is washed with three 2 ml portions of MeOH and dried.

EXAMPLE 4

(Z)-1-(Benzoyloxymethyl)-2-(chloromethyl)cyclopropane

Step A: Diethyl (Z)-cyclopropane-1,2-dicarboxylate

This material was prepared by a method similar to the literature procedures of G. B. Payne, *J. Org. Chem.*, 32, 3351 (1967) (for the diethyl ester), L. L. McCoy, *J. Am. Chem. Soc.*, 80, 6568 (1958) (for the monoethyl monomethyl diester) and W. von E. Doering and K. Sachdev, *J. Am. Chem. Soc.*, 96, 1168 (1974) (for the dimethyl ester). In a 3-necked flask equipped with addition funnel, thermometer, nitrogen bubbler, and mechanical stirrer, a suspension of 40.0 g (1 mole) of sodium hydride (60% dispersion in mineral oil) in 250 ml of dry toluene was stirred at room temperature as a mixture of 108.3 ml (100.1 g, 1 mole) of ethyl acetate and 84.5 ml (122.5 g, 1 mole) of ethyl chloroacetate was added dropwise. Even after addition of 0.5 ml of t-butanol, the reaction was not initiated until the temperature was raised to about 85° (oil bath). Within a few minutes at this temperature, the reaction became self-sustaining and the oil bath was removed. Hydrogen evolution continued as the temperature dropped, but after a few minutes an exotherm occurred (caution: vigorous foaming) and the reaction flask was immediately immersed in an ice bath. Cooling was continued until the mixture reached room temperature. The mixture was then added to cold $H_2O$ and extracted with ethyl acetate. The organic phase was dried with $MgSO_4$, filtered, and concentrated to give 220 g of amber residual oil. Fractional distillation afforded a total of 88.8 g of product, b.p. 98°–100° (4.5 mm); 90°–95° (2.5 mm), which was mainly cis-isomer, after collection of a small amount of the lower boiling trans-isomer. This was in agreement with the literature bp (83°–84° (1 mm): G. B. Payne, ref. cited above). The material was further purified by preparative high performance liquid chromatography (HPLC) through 2 Waters Prep Pak-500/silica columns (5 runs, elution with 93:7 hexane-ethyl acetate), giving 51.3 g (28%) of the cis-diester. Structure and purity were confirmed by 200 MHz NMR ($CDCl_3$) and analytical HPLC.

B. (Z)-1,2-Cyclopropanedimethanol

A 3-necked flask equipped with addition funnel, condenser, and nitrogen bubbler and containing 63.8 g (165 mmole) of lithium aluminum hydride was cooled in an ice bath as 160 ml of dry tetrahydrofuran was added. The ice bath was removed, and the mixture was stirred at ambient temperature as a solution of 20.5 g (110 mmole) of diethyl (Z)-1,2-cyclopropanedicarboxylate in 40 ml of tetrahydrofuran was added dropwise over 1.5 hours. The mixture was stirred at reflux for 2 hours and then overnight at room temperature. After cooling in an ice-methanol bath, the mixture was treated continuously with 37 ml of saturated aqueous ammonium chloride (added dropwise) and then with 40 ml of ethyl acetate. The insoluble salts were removed by filtration. The filtrate was concentrated, and the residue was taken up in ethyl acetate, dried with magnesium sulfate, filtered, and concentrated to give 6.32 g of oil. The salts which had been filtered off from the reaction mixture were re-suspended in a mixture of ethyl acetate and $H_2O$, neutralized with acetic acid, and stirred overnight at room temperature. The mixture was filtered, and the filtrate was extracted with more ethyl acetate. The organic solution was dried (magnesium sulfate), filtered, and concentrated to give an additional 2.56 g of product, for a total yield of 8.88 g (79%) of colorless oil. The 200 MHz NMR ($CDCl_3$) was in accord with the chemical shift values previously reported for this compound when obtained as a by-product from the diborane reduction of monomethyl cis-1,2-cyclopropanedicarboxylate [C. C. Shroff, W. S. Stewart, S. J. Uhm, and J. W. Wheeler, *J. Org. Chem.*, 36 3356 (1971)]. The compound has also been prepared by lithium aluminum hydride reduction of cis-1,2-cyclopropanedicarboxylic anhydride [E. Vogel, K. H. Ott, and K. Gajek, *Liebigs Ann. Chem.*, 644, 172 (1961)].

C. (Z)-2-(Benzoyloxymethyl)cyclopropanemethanol)

A mixture of 8.86 g (85 mmole) of (Z)-1,2-cyclopropanedimethanol, 10.3 ml (10.1 g, 128 mmole) of pyridine, and 90 ml of methylene chloride was stirred at 0° under nitrogen as 9.87 ml (11.95 g, 85 mmole) of benzoyl chloride was added dropwise. Stirring was continued at room temperature for 3 days. The mixture was then added to ice-water and extracted with ethyl acetate. The organic layer was backwashed twice with $H_2O$, dried with magnesium sulfate, filtered, and concentrated. The residual oil was chromatographed on a column of silica gel initially packed in hexane. Dibenzoate was eluted with 9:1 hexane-ethyl acetate, and subsequent elution with 3:1 hexane-ethyl acetate gave 5.6 g (32%) of the monobenzoyl ester. Structure and purity were confirmed by NMR ($CDCl_3$) and TLC (2:1 hexane-ethyl acetate).

D. (Z)-1(Benzoyloxymethyl)-2-(chloromethyl)cyclopropane

A solution of 0.99 ml (1.61 g, 13.6 mmole) of thionyl chloride in 6 ml of chloroform was added dropwise to a mixture of 2.8 g (13.6 mmole) of cis-2-(benzoyloxymethyl)cyclopropanemethanol, 1.07 g (13.6 mmole) of pyridine, and 5 ml of chloroform that was stirred at 0° under nitrogen The mixture was then heated at reflux for 1 hour under nitrogen. After concentration, the residual semi-solid was taken up in a mixture of diethyl ether and ethyl acetate and then filtered. Concentration of the filtrate gave 2.98 g (98%) of colorless oil which was suitable for use without further purification. Structure and purity were confirmed by NMR ($CDCl_3$).

EXAMPLE 5

1-[(Z)-2-(Hydroxymethyl)cyclopropylmethyl]thymine

A. 1-[(Z)-2-(Benzoyloxymethyl)cyclopropylmethyl]thymine

A mixture of 1.26 g (10 mmole) of thymine, 2.47 g (11 mmole) of (Z)-1-(benzoyloxymethyl)-2-(chloromethyl)-cyclopropane (from Example 4), 2.76 g (20 mmole) of anhydrous potassium carbonate, 1.50 g (10 mmole) of sodium iodide, and 15 ml of dimethyl sulfoxide was stirred under nitrogen at 80°–90° overnight. After removal of salts by filtration, the filtrate was concentrated under high vacuum. The residual oil was chromatographed on a column of silica gel initially packed in hexane. Elution with 1:1 hexane-ethyl acetate removed some dialkylated product, while elution with ethyl acetate provided 1.26 g (40%) of white solid. The 200 MHz NMR (DMSO-$d_6$) was in accord with the assigned structure. A small sample recrystallized from isopropanol had mp 153°–155°.

B.

1-[(Z)-2-(Hydroxymethyl)cyclopropylmethyl]thymine

A mixture of 927 mg (2.95 mmole) of 1-[(Z)-2-(benzoyloxymethyl)cyclopropylmethyl]thymine, 8 ml of 40% methylamine (aqueous) and 4 ml of methanol was stirred at reflux for 2 hours and then at room temperature overnight. The solution was then concentrated under high vacuum. Trituration of the residual oil gave a white solid, which was isolated by filtration. Following similar collection of a smaller second crop, the total yield was 319 mg (51%), mp 168°–169°. Structure and purity were confirmed by TLC (90:10:1 chloroform-methanol-water) and 200 MHz NMR (DMSO-$d_6$).

Analysis: Calculated for $C_{10}H_{14}N_2O_3 \cdot 0.1H_2O$: C, 56.65; H, 6.75; N, 13.21. Found: C, 56.64; H, 6.72; N, 13.08.

EXAMPLE 6

1-[(Z)-2-(Hydroxymethyl)cyclopropylmethyl]cytosine

Step A:

1-[(Z)-2-(Benzoyloxymethyl)cyclopropylmethyl]cytosine

A mixture of 1.22 g (11 mole) of cytosine, 2.72 g (12 mmole) of (Z)-1-(benzoyloxymethyl)-2-(chloromethyl)-cyclopropane, 1.52 g (11 mmole) of anhydrous potassium carbonate, 1.65 g (11 mole) of sodium iodide, and 15 ml of dimethyl sulfoxide was stirred under nitrogen at 70° for 3 days. The mixture was filtered to remove insoluble salts and then concentrated under high vacuum. The viscous residual oil was partitioned between ethyl acetate and water. The organic layer was dried with magnesium sulfate, filtered, and concentrated. The residual oil was chromatographed on a column of silica gel (elution with ethyl acetate). Fractions containing clean product by TLC were combined and concentrated to give 178 mg of glassy residue. Structure and purity were confirmed by TLC (90:10:1 CHCl$_3$-MeOH-H$_2$O) and 200 MHz NMR (DMSO-$d_6$).

Step B:

1-[(Z)-2-(Hydroxymethyl)cyclopropylmethyl]cytosine

A solution of 170 mg (0.57 mmole) of 1-[(Z)-2-(benzoyloxymethyl)cyclopropylmethyl]cytosine in 2 ml of methanol was treated with 3–4 drops of 1M methanolic sodium methoxide and then stirred at room temperature under protection from moisture for 1 day. Concentration to dryness gave a glassy residue. Trituration with isopropanol at 0° gave a white solid, which was collected by filtration. This material was dissolved in boiling ethyl acetate and filtered to remove a small amount of insoluble solid. Concentration of the filtrate followed by vacuum drying yielded 12 mg of white solid, m.p. 145°–146.5°. The product was homogeneous by TLC (ethyl acetate), and the structure was confirmed by 200 MHz NMR (DMSO-$d_6$).

Analysis for $C_9H_{13}N_3O_2 \cdot 0.1H_2O$: Calculated: C, 54.84; H, 6.75; N, 21.33. Found: C, 55.17; H, 6.68; N, 21.09.

EXAMPLE 7

1-[(Z)-2-(Hydroxymethyl)cyclopropylmethyl]-6-azauracil

Step A:

1-[(Z)-2-(Benzoyloxymethyl)cyclopropylmethyl]-6-azauracil

Stir a mixture of 10 mmole of 6-azauracil, 11 mmole of (Z)-1-(benzoyloxymethyl)-2-(chloromethyl) cyclopropane, 20 mmole of anhydrous potassium carbonate, 10 mmole of sodium iodide, and 15 ml of dimethyl sulfoxide under nitrogen at about 60°–90° overnight. Filter the mixture and concentrate the filtrate under high vacuum. Isolate the product from the residue by chromatography on silica gel.

Step B:

1-[(Z)-2-(Hydroxymethyl)cyclopropylmethyl]-6-azauracil

Stir a mixture of 3 mmole of 1-[(Z)-2-(benzoyloxymethyl)cyclopropylmethyl]-6-azauracil, 8 ml of 40% methylamine (aqueous), and 4 ml of methanol at reflux for about 2 hours. The mixture may be allowed to stir at room temperature overnight. Then, concentrate the solution. Crystallize the residue to obtain the desired product.

EXAMPLE 8

| Oil in Water Cream Base | |
| --- | --- |
| 1-[(Z)—2-(Hydroxymethyl)cyclopropylmethyl]thymine | 5.0 g |
| Lanolin, Anhydrous | 20.0 g |
| Polysorbate 60 | 4.0 g |
| Sorbitan Monopalmitate | 2.0 g |
| Light Liquid Paraffin | 4.0 g |
| Propylene Glycol | 5.0 g |
| Methyl Hydroxybenzoate | 0.1 g |
| Purified Water | to 100.0 g |

EXAMPLE 9

| Water Soluble Ointment Base | |
| --- | --- |
| 1-[(Z)—2-(Hydroxymethyl)cyclopropylmethyl]thymine | 0.5 g |
| Glycerol | 15.0 g |
| Macrogol 300 | 20.0 g |
| Polyethylene Glycol 1500 | 64.5 g |

EXAMPLE 10

| Tablet - (Total weight 359 mg) | |
| --- | --- |
| 1-[(Z)—2-(Hydroxymethyl)cyclopropylmethyl]thymine | 100 mg |
| Lactose | 200 mg |
| Starch | 50 mg |
| Polyvinylpyrrolidone | 5 mg |
| Magnesium Stearate | 4 mg |

For each of Examples 14–16, combine the listed ingredients by standard techniques.

What is claimed is:

1. A compound of the formula

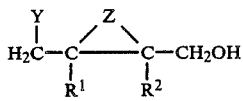

and the pharmaceutically acceptable salts thereof wherein Y is a member selected from the group consisting of uracil, cytosine, and thymine; $R^1$ is selected from hydrogen and alkyl of 1 to 4 carbon atoms; $R^2$ is selected from hydrogen, alkyl of 1 to 4 carbon atoms, and —CH$_2$OH; and Z is >CH$_2$ or >O.

2. A compound according to claim 1 wherein Y is a pyrimidin-1-yl group.

3. A compound according to claim 1 wherein Y is

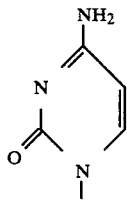

4. A compound according to claim 1 wherein Y is

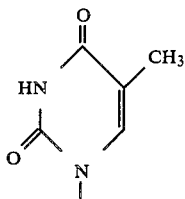

5. A pharmaceutical composition comprising an effective amount of a compound of claim 1 and a pharmaceutically acceptable carrier.

6. A method of treating virus infections selected from the group consisting of the herpes family and RNA viruses consisting of influenza and retroviruses in mammals comprising administering to a mammal in need of such treatment an effective amount of a compound of claim 1.

7. A compound of the formula

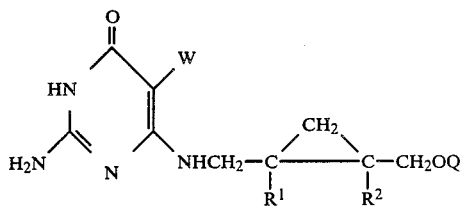

wherein Q is H or

W is H, —N=O,

or —NH$_2$; $R^1$ is hydrogen or alkyl of 1 to 4 carbon atoms; and $R^2$ is hydrogen, alkyl of 1 to 4 carbon atoms or —CH$_2$OH.

8. A compound according to claim 7 wherein Q is H.

* * * * *